United States Patent
Sanchez-Sava et al.

(10) Patent No.: US 10,779,534 B2
(45) Date of Patent: Sep. 22, 2020

(54) SEED DISINFECTION METHOD

(71) Applicant: ThermoSeed Global AB, Knivsta (SE)

(72) Inventors: Victor Manuel Sanchez-Sava, Grootebroek (NL); Gustaf Robert Forsberg, Örsundsbro (SE); Abraham Johan Ten Heuw, Tegelen (NL); Arvid Sven Georg Järbel, Uppsala (SE)

(73) Assignee: THERMOSEED GLOBAL AB, Knivsta (SE)

( * ) Notice: Subject to any disclaimer, the term of this patent is extended or adjusted under 35 U.S.C. 154(b) by 256 days.

(21) Appl. No.: 15/735,388

(22) PCT Filed: Jun. 10, 2016

(86) PCT No.: PCT/EP2016/063361
§ 371 (c)(1),
(2) Date: Dec. 11, 2017

(87) PCT Pub. No.: WO2016/198644
PCT Pub. Date: Dec. 15, 2016

(65) Prior Publication Data
US 2018/0177187 A1   Jun. 28, 2018

(30) Foreign Application Priority Data
Jun. 12, 2015  (EP) ................ 15171889

(51) Int. Cl.
*A01N 37/16* (2006.01)
*A01N 25/00* (2006.01)
*A01N 59/00* (2006.01)
*A01C 1/08* (2006.01)
*A01C 1/06* (2006.01)
*A61L 2/00* (2006.01)

(52) U.S. Cl.
CPC .......... *A01N 37/16* (2013.01); *A01C 1/06* (2013.01); *A01C 1/08* (2013.01); *A01N 25/00* (2013.01); *A01N 59/00* (2013.01); *A61L 2/0088* (2013.01)

(58) Field of Classification Search
None
See application file for complete search history.

(56) References Cited

U.S. PATENT DOCUMENTS

| | | | |
|---|---|---|---|
| 5,746,022 A * | 5/1998 | Brown | A01C 1/06 427/4 |
| 6,350,409 B1 | 2/2002 | Alness et al. | |
| 2013/0203849 A1* | 8/2013 | Ben Yehuda | A23L 19/105 514/557 |
| 2016/0066572 A1* | 3/2016 | Mathieu | A01N 37/02 514/546 |

FOREIGN PATENT DOCUMENTS

| | | |
|---|---|---|
| CN | 203840725 U | 9/2014 |
| EP | 2 153 876 A1 | 2/2010 |
| WO | 1997/038734 A1 | 10/1997 |
| WO | 2011/028115 A1 | 3/2011 |

OTHER PUBLICATIONS

International Search Report for corresponding International Application No. PCT/EP2016/063361 dated Jul. 28, 2017.
Written Opinion of the International Searching Authority for corresponding International Application No. PCT/EP2016/063361 dated Jul. 28, 2017.
Written Opinion of the International Preliminary Examining Authority for corresponding International Application No. PCT/EP2016/063361 dated May 11, 2017.
Written Opinion of the International Preliminary Examining Authority for corresponding International Application No. PCT/EP2016/063361 dated Aug. 29, 2017.
International Preliminary Report on Patentability for corresponding International Application No. PCT/EP2016/063361 dated Nov. 2, 2017.
Bang et al., "Combined effects of chlorine dioxide, drying, and dry heat treatments in inactivating microorganisms on radish seeds", Food Microbiology, vol. 28, 2011, pp. 114-118.
Beuchat et al., "Combined effects of water activity, temperature and chemical treatments on the survival of *Salmonella* and *Escherichia coli* O157:H7 on alfalfa seeds", Journal of Applied Microbiology, vol. 92, 2002, pp. 382-395.
Fosberg, "Control of Cereal Seed-borne Diseases by Hot Humid Air Seed Treatment", Doctoral Thesis, Mar. 5, 2004, pp. 1-49.
Fosberg et al., "Sensitivity of cereal seeds to short duration treatment with hot, humid air", Journal of Plant Diseases and Protection, vol. 110, No. 1, 2003, pp. 1-16.

* cited by examiner

Primary Examiner — Wayne A Langel
(74) Attorney, Agent, or Firm — Renner, Otto, Boisselle & Sklar, LLP

(57) ABSTRACT

The invention relates to a method for preparing disinfected seed, a use of a treatment composition, and an apparatus for disinfecting of seed. The method of the invention comprises contacting seed with a treatment composition comprising at least one disinfecting agent and/or a liquid component, and thereafter or at least partly simultaneously, exposing said seed to a treatment atmosphere for an exposure time of at least 1 second, wherein the treatment atmosphere has a relative humidity of at least 50% and a temperature of at least 40° C.

16 Claims, No Drawings

SEED DISINFECTION METHOD

This application is a national phase of International Application No. PCT/EP2016/063361 filed Jun. 10, 2016 and published in the English language, which claims priority to European Patent Application No. 15171889.7 filed Jun. 12, 2015.

The invention relates to a method for preparing disinfected seed, a use of a treatment composition, and an apparatus for disinfecting of seed.

Disinfection or disinfestation of plant seed before planting is important in order to reduce the impact of seed-borne pathogens and to improve crop yield and quality. Particularly desired is obtaining better control of superficial and internal bacteria. With current seed disinfection methods, such control is difficult or impossible to obtain. A further desire is to reduce the use of harmful substances such as some biocides because of environmental and health concerns. Hence, using smaller amounts and/or less harmful biocides is desirable.

WO-A-97/38734 relates to a heat treatment process for disinfection of seeds from pathogens and other undesirable fungi and bacteria, involving supplying to the seeds non-water-borne heat while regulating the treatment time and temperature with regard to the condition and moisture content of the seeds, in such a way that the seeds are heated from outside while evaporation of moisture from the surface of the seed and, owing to that, cooling of the same is prevented and no changes in the moisture content occur. In the example, the degree of disinfection was determined based on the presence of pathogenic fungi. The method leaves room for improvement of the disinfecting effect on seed-borne bacteria in a number of plant species.

Bang et al. (*Food Microbiology* 2011, 28, 114-118) describe a study on the combined effects of chlorine dioxide, drying and dry heat treatments in inactivating microorganisms on radish seeds.

Beuchat et al. (*Journal of Applied Microbiology* 2002, 92, 382-395) discloses a treatment of alfalfa seeds inoculated with *Salmonella* or *E. coli* involving heating in water and chemical solutions, but no treatment in a humid atmosphere.

Forsberg, *Doctoral thesis,* 2004, Swedish University of Agricultural Sciences, Uppsala), is concerned with the treatment of cereal seed using hot, humid air, or aerated steam. The seed is not contacted with a treatment composition comprising at least one disinfectant agent and/or a liquid component.

EP-A-2 153 876 discloses an apparatus wherein seeds are transported over a conveyor belt and are sprayed with water in a first chamber and subjected to dry air in a subsequent chamber.

CN-A-203 840 725 relates to an agricultural seed sterilising and drying device, wherein the seed is treated in three separated chambers.

Forsberg et al. (*Zeitschrift für Pflanzenkrankheiten and Pflanzenschutz* 2003, 110(1), 1-16) describe tests wherein cereal seeds are subjected to short treatments with hot humid air. The influence which variable seed moisture contents have on the heat tolerance of the seed is studied in this article.

An object of the present invention is to provide a method for preparing disinfected seed that addresses one or more of the above-mentioned problems and desires at least in part. It has surprisingly been found that this objective can be met by contacting seed with a treatment composition in combination with exposing said seed to a treatment atmosphere.

Accordingly, the invention relates in a first aspect to a method for preparing disinfected seed, comprising contacting seed with a treatment composition comprising at least one disinfecting agent and/or a liquid component; and thereafter or at least partly simultaneously, exposing said seed to a treatment atmosphere for an exposure time of at least 1 second, wherein the treatment atmosphere has a relative humidity of at least 50% and a temperature of at least 40° C.

The method advantageously provides for improvements of disinfecting seed from bacteria, especially seed-borne bacteria. In addition, the method allows for using smaller amounts and/or less harmful substances such as biocides. The method may in addition provide for a disinfecting effect on seed-borne pathogenic fungi and other pathogens different from bacteria, for example nematodes and seed-borne insects. Moreover, the method allows for seed disinfection without significantly affecting the seed quality or the germination properties.

The term "seed" as used herein includes but is not restricted to a ripened ovule of gymnosperms and angiosperms, which contains an embryo surrounded by a protective cover, the seed coat (testa). Some seeds comprise a pericarp or fruit coat around the seed coat. In practical terms, the term "seed" is used to include anything that can be planted (sown) in agriculture to produce plants, such as true seeds, rootstock, plant cuttings and plant parts such as a tuber or bulb. Preferably, however, the term "seed" refers to its normal meaning in the art, namely the fertilised ripened ovule of a flowering plant containing an embryo and capable normally of germination to produce a new plant.

The term "disinfection" of plant seed includes for instance removing, killing, rendering harmless and/or reducing the impact of a pathogen, in particular bacteria and fungi. The pathogens may also be nematodes and seed-borne insects, including eggs thereof. Preferably, the pathogens are bacteria. Rendering harmless a pathogen includes for instance causing the pathogen to be not capable of infecting the plant. Some examples of methods for preparing disinfected seed include seed treatment methods providing for a reduction in the percentage of infected seeds, and methods providing a reduction in the number of colony forming units.

The term "disinfection" is not used as implying a restriction on the objects which are disinfected, in particular, the plant seed may be considered as living or non-living.

The term "disinfected seed" includes, and is not restricted to, seed for which a reduction in the number of infected seedlings and/or colony forming units for one or more pathogens is observed compared to untreated seed. Hence, a disinfected seed may still comprise a number of living pathogens. An example of disinfected seed is seed in which the pathogenic inoculum for at least one type of pathogen is at least partly rendered harmless or less harmful, for instance by killing, removal or inactivation thereof.

The term "disinfecting agent" refers to a compound or composition exhibiting a disinfecting effect.

The term "treatment atmosphere" as used herein includes a gaseous phase having a temperature and relative humidity to which seed is exposed. The term "relative humidity" as used herein refers to the ratio of the partial pressure of water vapour in the gaseous phase to the saturated vapour pressure of water at the temperature of the treatment atmosphere. The term "exposure time" as used herein refers to the duration of the exposure of the seed to the treatment atmosphere.

The term "dormancy" for bacteria includes at least a state of low biological activity, low metabolic activity, or rest. The term also includes a "viable but non-culturable" state. The term includes bacteria which do not grow and are not culturable on standard media (e.g. agar), but still exhibit metabolic activity or potential to show such activity later (resting stages), indicating that the bacteria are viable. Generally, favourable conditions can result in reactivation of the bacteria. Such reactivation is sometimes referred to as resuscitation.

In general most commercial seed is dried, for instance, to an absolute moisture content of 4.5-8% (vegetables and flowers) and between 8-11% for agronomical seed and tree seed, and generally 10-16% for cereals. The low moisture content in commercial seed is provided by a drying process in the field or after harvest, which is often applied to assure proper shelf life of the seed.

Bacteria may possibly enter a dormant state and/or develop a protection via a biofilm upon environmental stress, such as drying and low temperatures. Hence, the seed, whether dried or not, may contain seed-borne and/or seed-transmitted bacteria in a state of "dormancy". Bacteria in this state may be less sensitive to environmental changes. For instance, dormant bacteria may be able to survive drastic environmental changes in temperature and pH or oxygen deprivation that would be lethal to bacteria not in a dormant state. As a result, general seed disinfection methods may be less effective against dormant bacteria than for active bacteria.

Without wishing to be bound by way of theory, the advantageous results of the combination of a treatment composition and a treatment atmosphere may at least partly be obtained by virtue of one or more of the following effects. For example, contacting seed with a treatment composition may cause reactivation of dormant bacteria. In this way, a subsequent exposure of the seed to a treatment atmosphere may be more effective since fewer bacteria are dormant during the exposure to a treatment atmosphere. Similarly, a disinfecting agent may be more effective against active bacteria. Disinfecting agents which have a stronger disinfecting effect at higher temperature, for example water and peroxides, can have synergistic effect with the treatment atmosphere. Increased moisture content of cells of pathogens may facilitate chemical and physical reactions including reactions that deteriorate functions of the pathogen.

Alternatively or in addition, a higher temperature during the exposure of the bacteria to the tre1atment atmosphere may make the bacteria more liable to action of a disinfecting agent. Alternatively or in addition, a disinfecting agent may be more active or effective at higher temperatures. Such disinfecting agent may be applied to the seed by the treatment composition.

Alternatively or in addition, the treatment composition may mitigate the effect of air pockets in seed endosperm. Such air pockets can be formed by air trapped in (or between cell membranes) pockets in seed, especially in dried seed. Also pores of some seed may provide air in intra-cellular space or air pockets. Since air is not a good heat conductor, this may contribute to a reduced effect of exposure to the treatment atmosphere. The disinfecting effectivity of the exposure to a treatment atmosphere may be increased by at least partially replacing air in such air pockets and/or pores by a liquid treatment composition, in particular water, since liquids are better heat conductors. This includes wetting of such pores or pockets by treatment composition. This may increase the speed of heat transmission within the endosperm and may also improve the effect against any bacteria located within the air pockets—reducing heath time exposure to the embryo—which can be lethal. Filling or wetting of the air pockets may also improve contact between a disinfecting agent and bacteria within such pores, increasing the effect of the disinfecting agent. To increase efficiency thereof, the method preferably comprises stirring or vibrating the seed with treatment composition (for example with ultra-sound) during or after contacting with treatment composition.

Alternatively or in addition, contacting with a treatment composition comprising a liquid component may result in wetting of the surface of the seed. This may help mitigating any insulating effect of the roughness of some seed, which may otherwise limit the effectivity of the exposure to a treatment atmosphere. A treatment composition comprising a surfactant may provide improved wetting. A surfactant may also help delivering disinfecting agent effectively into the seed endosperm. Wetting of the seed may further increase control of the process, by delivering heat at a more constant temperature, and also for cooling after exposure to a treatment atmosphere. Quick and sufficient cooling is important for seed quality and germination properties.

Irrespective of the above mentioned effects, which do not limit the invention by way of theory, the examples demonstrate a synergistic effect of a treatment composition and treatment atmosphere resulting in more efficient disinfection. Even with just water as treatment composition, an advantageous interaction with exposure to a treatment atmosphere was shown.

Accordingly, the seed may comprise dormant bacteria before the contacting with a treatment composition and optionally the seed is provided as dried seed. Preferably, the method comprises reactivating at least some dormant bacteria by the contacting with a treatment composition and/or the exposing to a treatment atmosphere, more preferably by the treatment composition. Preferably, the method comprises subjecting reactivated bacteria, and/or other pathogens, to a disinfecting agent and/or to heat by exposure of the seed to the treatment atmosphere. In such preferred method, the heat exposure may have a disinfecting effect on reactivated pathogens as well as on other sensitive pathogens.

Preferably, the treatment composition comprises water and/or is a liquid. To improve wetting, the treatment composition preferably comprises a surfactant. This may also provide for better penetration of treatment composition within the seed in any air pockets and/or pores of the seed. Surfactants may also contribute to bacteria detachment form the seed, in particular in case of bacteria attaching to seed surface by hydrophobic interaction. This is in particular advantageous for crops having seed with a hydrophobic seed surface. For example some seed have a surface comprising epicutular waxes. Such waxes may comprise alkanes, long-chain alcohols, ketones, and/or esters of long-chained fatty acids. Seed of some crops comprise hydrophobic proteins on their seed coats. Examples include soybean and rapeseed. For such crops, a treatment composition comprising a surfactant is particularly advantageous.

Preferably, a liquid treatment composition comprising water and surfactant is supplied to the seed in an amount providing at least 10 g water per kg seed and/or at a temperature of at least 20° C.

Preferably, the method involves wetting of the seed by liquid treatment composition and/or saturating at least part of the seed intra-cellular space (pores) and/or air pockets with liquid treatment composition. This may provide for more effective delivery of heat to pathogens in these air pockets and pores, in view of the higher thermal conductivity of water and liquids as compared to air. Filling of pores or air pockets may for instance be determined by freezing followed by microscopy. Hence, preferably, during exposure of the seed to a treatment atmosphere pores and/or pockets of the seed contain liquid treatment composition, more preferably are essentially filled with such composition. Preferably, the method comprises exposing the seed to a treatment atmosphere while pores and/or pockets of the seed contain liquid treatment composition. Preferably, such liquids comprise a disinfecting agent. Preferably, the method comprises stirring or vibrating (for example with ultrasound) during or after contacting with treatment composition. This may provide for instance increased efficiency of wetting of the seed and/or filling or wetting of the air pockets.

The seed to be disinfected is usually capable of germinating. Suitable seeds include non-germinated, preferably non-primed seeds. Optionally, the seed may be deprived of husk (de-husked seed or de-hulled seed). Preferably, directly prior to the contacting with a treatment composition and/or to the exposure to the treatment atmosphere, the seeds have a temperature of −10° C. to +30° C., more preferably 0-25° C., for example 10-25° C., and are optionally kept above 5° C., 10° C., or 15° C. during the method until the optional cooling step. Optionally, the method begins with opening a packaging containing seed or by providing a seed lot. The method may also comprise providing seed to a seed treatment unit prior to said contacting, wherein the unit comprises for instance a chamber for seed with at least one inlet for the treatment composition. The method optionally comprises recycling of the treatment composition. The seed as supplied may comprise seed-borne pathogens, such as bacteria, in particular dormant bacteria, or may be susceptible or at risk of containing such bacteria.

The method involves contacting seed with the treatment composition. Preferably, the contacting with the treatment composition is at least in part carried out at a temperature of less than 50° C. or less than 40° C., such as 5-50° C. Preferably, during the contacting the seed and/or treatment composition has a temperature of less than 50° C. or less than 40° C., such 5-50° C., most preferably 15-35° C. Preferably, the treatment composition is applied at controlled temperature. This advantageously provides high efficiency and/or reliability. Preferably, the treatment composition is applied at least 15° C. or at least 20° C. Preferably, the seed is contacted with the treatment composition for a contacting time of at least 10 seconds, such as at least 1 minute, or at least 5 minutes or at least 10 minutes, and for example less than 24 hours, such as less than 60 minutes, for instance 10-30 minutes or 60-300 seconds. The seed can be contacted with the treatment composition for example by soaking or immersing the seed in the treatment composition, or by spraying, dripping or flowing the treatment composition onto the seed, or by controlled moisture increase, condensation, imbibition, or by washing the seed with the seed treatment composition. A gaseous treatment composition may for instance be blown over the seed. A powdery treatment composition may for instance be admixed to the seed.

Seed can optionally be provided in a bag or basket, on a plate, or in another form of container during the contacting, and also on a moving belt. The method may optionally result in absorption of treatment composition by seed. Absorption of the treatment composition into the seed may provide for improved antimicrobial efficacy, especially against internal bacteria. Preferably, the weight of the seed increases during the contacting with the treatment composition by at least 1.0%, based on the difference in seed weight prior and after said contacting, with removal of excess treatment composition, divided by the weight prior to contacting. Removal of excess treatment composition may for example involve wiping the seed dry. The weight increase can for instance be 0.10-25%, such as at least 1.0%, at least 2.0%, for instance less than 20%, for instance 2-15% and/or 15-25%. Hence, seed may absorb treatment composition in an amount of for instance at least 5% or at least 10% of their weight, such as 15-25% or 20-25%.

The contacting may also result in some swelling of the seed, for instance a volume increase of at least 0.5% or at least 2.0%.

The method comprises exposing seed to the treatment atmosphere, generally after the contacting of the seed with the treatment composition, or at least partly simultaneously therewith.

In principle, the method may comprise two or more steps of contacting with a treatment composition, wherein the treatment composition can be the same or different. The method may also comprise any additional steps of contacting of seed with compositions at any stage of the method, either with treatment compositions having the same or different disinfecting agent and/or liquid component, or with compositions comprising neither disinfecting agent nor liquid component.

Preferably, when the exposure to the treatment atmosphere is subsequent to contacting the seed with treatment composition, the method comprises removing at least part of the treatment composition from the seed prior to the exposure to a treatment atmosphere. For example, the method may comprise removing excess treatment composition. This is especially advantageous in case the treatment composition is phytotoxic. Removing the treatment composition may comprise centrifuging, evaporative drying, for instance pat drying (e.g. gentle drying with a towel or similar fabric), wiping, blowing, and draining by gravity or pumping. In case the treatment composition comprises a disinfecting agent, the removal may comprise for instance rinsing (preferably with water). For example, the method may comprise rinsing with water for 10 seconds to 10 minutes. Seed can also be centrifuged, for instance for 10 seconds to 5 minutes, optionally in combination with rinsing.

The treatment composition comprises at least one disinfecting agent and/or a liquid component and may comprise additional components. The liquid component is preferably water. For example, the treatment composition may essentially consist of water (such as more than 99 wt. %), for instance can be tap water. Hence, the method may comprise contacting the seed with water.

The treatment composition may be applied for example in liquid form, for example the form of a solution, suspension, dispersion, emulsion or foam, and also as spray, mist, or aerosol, preferably aqueous ones. The treatment composition may also be gaseous or solid. For instance, the treatment composition may comprise ozone or a powder. Generally, the treatment composition is flowable, including fluid (liquid or gaseous), or granular, preferably the composition is liquid. Preferably, the treatment composition is liquid, comprises water and/or comprises a surfactant.

Preferably, the treatment composition is in liquid form and comprises water and more preferably a surfactant. For treatment compositions comprising hydrophobic components, in particular as disinfecting agent, such as some carboxylic acids, adding a surfactant is preferred. The surfactant may improve the efficacy of hydrophobic disinfecting agents by improving contact between such agents and the bacteria.

For example anionic, cationic, zwitterionic and non-ionic surfactants can be used. Preferably the surfactant is an organic compound comprising a hydrophilic group. Examples include linear alkylbenzenesulphonates, lignin sulphonates, fatty alcohol ethoxylates and alkylphenol ethoxylates. Some possible surfactants have anionic functional groups such as sulphate, sulphonate, phosphate and carboxylates, in particular alkyl carboxylates, for instance dodecyl sulphate salts, and alkyl-ethers thereof. Cationic surfactants include primary, secondary, or tertiary amines and quaternary ammonium salts, in particular aromatic quaternary ammonium salts. Other surfactants are zwitterionic compounds having a phosphate anion with amine or ammonium. Polyoxyethylene and polyoxypropylene glycol alkyl ethers can be used, as well as for example glucoside alkyl ethers, glycerol alkyl ethers, polysorbate, block copolymers of polyethylene glycol and polypropylene glycol, and polyethoxylated tallow amine. The skilled person can apply suitable amounts of surfactant, such as at least 1 ppb or at least 10 ppb (parts per billion by weight) or at least 100 ppb or at least 1.0 ppm, at least 10 ppm, at least 20 ppm (parts per million by weight), at least 0.010 wt. %, at least 0.10 wt. %, at least 1.0 wt. %, based on total weight of the treatment composition, or for example concentrations providing at least 1 μm or at least 1 mg or at least 10 mg, at least 0.10 g, at least 1.0 g, at least 5.0 g, or at least 10 g per kg seed.

Preferably, the treatment composition comprises rhamnolipids. These can act as surfactant. For instance, glycolipids can be used having a glycosyl head, a rhamnose moiety, and a fatty acid tail such as a 3-(hydroxyalkanoyloxy)alkanoic acid (HAA) fatty acid tail. A concentration of for example between 10 ppb and 100 ppm can be used, such as 1-100 ppm by weight in the treatment composition, for instance 0.0010-0.10 ml/l.

In case the treatment composition comprises water, the seed is preferably contacted with the treatment composition for at least 10 seconds, such as at least 30 seconds or at least 60 seconds. More preferably, the seed is in contact with the treatment composition for 10 minutes or more, such as 20-60 minutes or 20-40 minutes. It is preferred that the water has a temperature of less than 50° C., more preferably less than 40° C., such as 20-40° C. The treatment composition is preferably is supplied as liquid.

For treatment composition comprising water, the seed is preferably wet at the beginning of the exposure to the treatment atmosphere and preferably comprises at least 0.10% water adhering to the seed, based on total weight of the wet seed, more preferably at least 1.0% or at least 2%, generally less than 10%. The amount water adhering to the seed can be measured by removal thereof as is conventional, e.g. by gently wiping the seed dry. Preferably, the seed has a moisture content of at least 5% or at least 8%.

Preferably, the treatment composition comprises a disinfecting agent, preferably selected from the group consisting of organic acids, carboxylic acids, alcohols, aldehydes, oxidising agents such as peroxides and peroxy acids, phenolic compounds, quaternary ammonium compounds, silver and silver compounds, including silver ions and colloidal silver, chlorine and chlorine compounds, and iodophors.

The treatment composition may comprise a disinfecting agent. For example, the treatment composition may comprise at least at least 0.010% or at least 0.10%, or at least 1.0% disinfecting agent, based on total weight of the treatment composition. Preferably, a disinfecting agent is supplied to the seed in an amount of at least 10 mg or at least 1.0 g per kg seed, such as at least 5 g per kg seed. Preferably, the disinfecting agent comprises, or consists of, an antimicrobial compound, more preferably it has a bactericidal and/or bacteriostatic effect. Fungicidal and sporicidal compounds are also attractive as disinfecting agents.

Alcohols include in particular substituted or unsubstituted alkyl, cycloalkyl, aryl and alkaryl alcohols, for example with 2-20 carbon atoms. Some example include unsubstituted straight or branched alky alcohols, for instance with 2-6 carbon atoms, for instance ethanol and/or (iso)propanol. The treatment composition may optionally comprise a wetting agent, such as an alkyl carboxyl acid. Combination with exposure to a treatment atmosphere having a relative humidity as specified may facilitate diffusion through cell membranes, thereby enhancing efficacy.

Some examples of phenolic compound include phenol, ortho-phenylphenol, ortho-benzyl-para-chlorophenol, thymol, chloroxylenol. Some examples of suitable aldehydes include monoaldehydes and dialdehydes, for instance formaldehyde, glutaraldehyde, ortho-phthalaldehyde. Some examples of suitable quaternary ammonium compounds include alkyl, cycloalkyl, aryl, alkaryl quaternary ammonium compounds, for instance comprising benzalkonium, cetyl trimethylammonium, didecyldimethylammonium, cetylpyridinium, benzethonium, and halide salts thereof, in particular chlorides. Silver compounds include silver dihydrogen citrate and chelated forms of silver. Polyaminopropyl biguanide can also be used. Iodophors include combinations of iodine and a solubilising agent or carrier, for example povidone-iodine.

Some examples of oxidising compounds include chlorine compounds and oxygen compounds, for instance hypochlorite, chloramine, chlorine dioxide, perchloric acid, peroxide compounds, hydrogen peroxide, peroxy acids, peracetic acid, performic acid, potassium permanganate, and potassium peroxymonosulphate, and aqueous solutions thereof. In addition, ozone gas can be used as disinfecting agent. Some examples of carboxylic acids include α-hydroxy acids, malic acid, citric acid, lactic acid, adipic acid, tartaric acid, acetic acid, peracetic acid, benzoic acid, sulphamic acid, and oxalic acid.

Optionally, the treatment composition has a pH of less than 6, less than 5, or even less than 4, contributing to bactericidal effect.

A disinfecting agent preferably has low or no phytotoxicity at the applied amount and preferably is not persistent. Preferred are hence hydrolysable agents. The phytotoxicity is known for many commercially available agents and can be tested according to routine methods. Optionally, the treatment composition can comprise for instance nutrients for the seedling.

The treatment composition may for example comprise a peroxide compound such as hydrogen peroxide, for instance at least 0.10%, at least 0.50%, or at least 1.0% by total weight of the treatment composition. The composition typically contains less than 20 wt. % peroxide and preferably less than 5.0 wt. % in view of the effect on germination properties. Suitable commercial peroxide solutions are available. The peroxide solution may contain the usual stabilisers for the peroxide as appropriate. The composition is preferably an aqueous solution and may further comprise an organic acid, such as peracetic acid and/or acetic acid, and/or a surfactant. The treatment composition may for instance comprise peracetic acid and hydrogen peroxide in a 2:1 to 1:10 mass ratio, preferably 1:1 to 1:5, more preferably 1:1.2 to 1:4 and further optionally comprise a surfactant and/or solubilising agent, preferably with a concentration hydrogen peroxide of 1.0-10 wt. %, more preferably 2.0-7.0 wt. %.

The treatment composition, whether or not comprising water and/or disinfecting agent, are preferably supplied to the seed in an amount of at least 0.1 g or at least 1.0 g or at least 10 g or at least 0.1 kg seed per kg treatment composition.

Preferably, the treatment composition comprises water and is supplied to the seed in an amount providing at least 100 g water per kg seed, or at least 1.0 kg water per kg seed, such as at least 2 kg water or at least 5 kg water per kg seed. For instance, seed can be soaked in treatment composition in a ratio of at least 5 parts liquid per 1 part seed, or at least 10 parts liquid, by weight. In a continuous process, the ratio applies to the amount water and seed supplied per minute.

Contacting the seed with the treatment composition may results in an increase of the moisture content of the seed. For example, the moisture content of the seed may be increased by 5% or more, such as 10% or more, or 20% or more.

In accordance with the invention, the seed is exposed to the treatment atmosphere after or at least partly simultaneously to contacting the seed with the treatment composition. In case the seed is exposed to the treatment atmosphere after contacting the seed with the treatment composition, then it is preferred that seed is exposed to the treatment atmosphere 30 minutes or less from having contacted the seed with the treatment composition, such as 15 minutes or less, preferably 10 minutes or less, more preferably 1-5 minutes.

The method comprises exposing the seed to a treatment atmosphere for an exposure time, wherein the treatment atmosphere has a relative humidity and temperature. The treatment atmosphere has a relative humidity of at least 50% and a temperature of at least 40° C.

Preferably, the treatment atmosphere has a relative humidity of at least 60%, more preferably at least 70%, even more preferably at least 80%, or at least 90%. Preferably, the treatment atmosphere has a relative humidity of 100% or less. Using a treatment atmosphere with such relative humidity advantageously allows reducing the amount of evaporation from the seed during the processing. In some aspects, it enhances certain controlled water absorption which can take place either from the vapour directly or from a thin layer of water condensed on the seed surface.

The treatment atmosphere can be saturated or supersaturated with water vapour. Optionally, the treatment atmosphere can comprise superheated steam. The treatment atmosphere comprises preferably a mixture of air and water vapour. The treatment atmosphere can for example be prepared by mixing air and steam, and is for example provided in the form of a stationary or flowing gaseous phase, preferably a gas stream, for instance comprising air and water vapour.

The treatment atmosphere can reach a relative humidity of for example 100%, at least in parts of the seed bed. The method can comprise for example transferring heat from steam comprised in the treatment atmosphere to the seed. The method optionally comprises condensation of water vapour from the treatment atmosphere on the seed, for example temporarily condensation. This can advantageously contribute to efficient heat transfer to the seed. The condensation may result in the formation of a thin liquid film of water on the seed. The film can for example be absorbed to the seed surface in a controlled way. The method optionally comprises evaporating such thin liquid film of water during the preferred phase of cooling and optionally drying. The method may also optionally comprise direct transfer of heat and moisture from the air to the seed, without condensation of water.

Without wishing to be bound by way of theory, the formation of a thin liquid film of water may contribute to the effect of the treatment composition and/or disinfecting agent therein. In particular, the film may ensure that components of the treatment composition remain on the seed and/or inside the seed, for instance in the thin liquid film, and/or beneath the seed surface. Evaporation and removal of components may be reduced by a thin liquid film and/or the humidity. Higher temperature may contribute to activity of a bactericidal and/or bacteriostatic component, such as a peroxide compound.

Optionally, the treatment composition is present on and in the seed during at least part of said exposure to said treatment atmosphere in an amount of at least 1.0 g treatment composition per kg seed, such as at least 10 g per kg seed. For example, the seed may comprise at least 0.10 g or at least 1.0 g or at least 10 g or at least 50 g disinfecting agent per kg seed during the exposure to a treatment atmosphere. The amounts include absorbed treatment composition. This can provide for a beneficial effect of the treatment atmosphere on the efficacy of the disinfecting agent.

Preferably, the disinfecting agent if used exhibits bactericidal and/or bacteriostatic activity, during said exposure to a treatment atmosphere, preferably bactericidal activity. Also in this way the combination of contacting with a treatment composition and exposure to a treatment atmosphere may contribute to an improved effect against bacteria.

Optionally, the treatment atmosphere comprises a disinfecting agent, preferably a vapour, mist and/or aerosol of a disinfecting agent. For instance, hydrogen peroxide vapour or mist can be supplied to the seed during said exposure. Natural oils and volatile natural disinfectants, such as tea tree oil may also be added.

Preferably, the treatment atmosphere to which the seed is exposed has a temperature of at least 50° C. or at least 55° C. or even at least 80° C., typically less than 100° C., or less than 85° C. Also possible are temperatures of more than 100° C., for instance in combination with pressures higher than 1 bar, for example at least 1.1 bar, at least 1.5 bar, at least 2 bar or at least 5 bar.

Preferably, the temperature and/or the dew point temperature of the treatment atmosphere are kept substantially constant, such as within a range of ±5° C. (increase or decrease of each not more than 5° C., total width 10° C.), more preferably ±2° C. or ±1° C. or narrower, even more preferably in a range of ±0.5° C., during said exposure to a treatment atmosphere.

Preferably, the exposure time, and hence duration of a step of exposing the seed to the treatment atmosphere, is 300 minutes or less, or 120 minutes or less, more preferably 30 minutes or less, 20 minutes or less, or 10 minutes or less. Some non-limiting example exposure times are at least 1 second or at least 10 seconds, for example 10 seconds to 10 minutes, or 30-300 seconds, or 60-300 seconds, or 90-180 seconds. Preferably, the seed is continuously exposed to a treatment atmosphere for such period. A further preferred method comprises a pulsed exposure to the treatment atmosphere, comprising at least two, such as at least three or four or five or ten or more exposures to such treatment atmosphere, for example each of 1-60 seconds, interspersed with exposures to cooler atmospheres for example for 1-60 seconds. Such pulsed exposure can for example be carried out by alternating cooling and heating. Preferably, the treatment atmosphere comprises a gas stream, having a flow rate between 0 and 5 m/s just before and/or after a seed layer, for instance 0.5-3 m/s or 1.0-2.5 m/s.

Optionally, the method for preparing disinfecting seed comprises a batch process and/or a (semi-)continuous process for exposure to the treatment atmosphere. In a batch process, the seed is preferably provided in a processing chamber and exposure of the seed to the treatment atmosphere preferably comprises introducing a treatment atmosphere into the processing chamber wherein the seed is present. The batch treatment chamber is preferably a closed vessel with injection of the moist air or steam prior, afterwards or simultaneously with the introduction of the seeds. Another preferred chamber is an open vessel where the treatment gas is flowing through the vessel from an entrance to an exit. The vessel is preferably equipped with a device or arrangement for mixing that can move around seeds and gas for increased uniformity. Preferably, the exposure takes place during fluidisation of the seeds, hence in a fluidised bed. Another preferred seed bed is a thin layer fixed bed.

In a continuous process, the exposure of the seed to the treatment atmosphere is preferably carried out by moving the seed on a seed bed through a processing chamber comprising the treatment atmosphere. The motion of the seeds can be carried out for example through pneumatic transport, through gravity transport, through fluidisation or through mechanic conveying (for example a screw auger, a shaking/vibrating conveyor, chain conveyor, belt conveyor or a rotating drum or an elevator) or a combination of such. The duration of the exposure of the seed to the treatment atmosphere is typically equal to the residence time of the seed in the processing chamber and can be controlled for example through the speed of a moving seed bed, such as a chain conveyor through the processing chamber.

Typically, the seed is evenly exposed to the treatment atmosphere. Preferably, the surface of the seed is evenly exposed such that generally all parts of the surface of a seed are exposed to the treatment atmosphere for substantially the same time. In a continuous process, the seed is preferably exposed to the treatment atmosphere while the seed is on or in a vibrating fluidised continuous bed. The transport rate is typically controlled by a built-in chain conveyor. The seed can furthermore be provided as a layer on a moving seed bed, wherein a treatment gas stream as treatment atmosphere can be blown from below through the moving seed bed into a processing chamber.

To increase energy efficiency, preferably the exposure to a treatment atmosphere is carried out in a system that is closed with respect to a gas stream, preferably by recirculating the treatment atmosphere in a closed loop. Also the gas stream used for preferred cooling and/or drying can be recirculated for recovery of part of the heating energy, potentially combined with an air moisture trap to reduce the air humidity. Preferably, the heating energy can also be recovered by heat exchange between an inlet channel for treatment atmosphere and exhaust gas.

Preferably, the treatment atmosphere has one or more, preferably all of: a temperature of 50-100° C.; a relative humidity of at least 75%, and an exposure time of from 1 second to 10 minutes, preferably of 5-300 seconds.

For cereals, many vegetable seeds, rice and other crops, the treatment atmosphere preferably has a temperature of 50-95° C., more preferably 55-80° C., more preferably in combination with a relative humidity of 70-100%, more preferably 80-100%, even more preferably 90-100%; most preferably in combination with an exposure time of 30-600 seconds, more preferably 60-300 seconds. An exposure time of 2-5 minutes, for example about 2 minutes (60-180 seconds), is preferably used in combination with a 55-80° C. treatment atmosphere, for instance for cereals and vegetable seeds. For alfalfa seed and other more heat tolerant species, the temperature is preferably in the range of 60-90° C., preferably in combination with the same preferred relative humidity and exposure times.

Preferably, the seed has a core temperature of 20-50° C. during at least part of the exposure time, preferably at the end of the exposure time. Preferably, the temperature in the core of the seeds is kept below 90° C. during the entire exposure and/or disinfection method, more preferably below 70° C. or below 50° C., to ensure good seed quality. Preferably, the water content of the seed changes, preferably increases, during the exposure time by less than 10 wt. % based on the weight of the seed prior to exposure, more preferably by 1-5 wt. %. Optionally, the water content is not substantially changed. A limited change of water content may provide advantages, for instance provide better germination or breaking seed dormancy.

In a non-limiting, advantageous embodiment, the method preferably comprises contacting seed with said treatment composition prior to said exposure, and the treatment composition comprises an aqueous solution comprising a surfactant, at least 0.10 wt. % of one or more carboxylic acids and at least 0.10 wt. % of one or more peroxide compounds, based on total weight of the treatment composition. Preferably, in such preferred method the treatment atmosphere has a temperature of 50-100° C. and a relative humidity of at least 80%, and the exposure time is from 30 seconds to 10 minutes. Contacting with the treatment composition preferably is carried out at 15-25° C. and/or has a duration of 60-300 seconds, such as 60-180 seconds, for instance by soaking, optionally followed by rinsing with water for instance for 10-300 seconds. The seed may be centrifuged for instance for 10-60 seconds and thereafter exposed to a treatment atmosphere. The aqueous solution for instance has a pH of 6 or lower.

The seed is, for example, seed of an agricultural crop including vegetables. Some examples of suitable seed further include vegetable seed, herb seed, wildflower seed, ornamental seed and grass seed and tree and bush seeds. The seed can be of the order of Monocotyledoneae or from the order of Dicotyledoneae. Some examples from the order of Monocotyledoneae are rice seed and wheat, *Triticum aestivum*. Some examples of suitable seed include seed of soybean, cotton, corn, peanut, maize, wheat, barley, oat, rye, triticale, mustard, sunflower, sugar beet, safflower, millet, chicory, flax, rapeseed, buckwheat, tobacco, hemp seed, alfalfa, signal grass, clover, sorghum, chick pea, beans, peas, corn salad (*Valerianella locusta*), and vetch. Some examples of suitable vegetable seeds include asparagus, chives, celery, leek, garlic, beetroot, spinach, beet, curly kale, cauliflower, sprouting broccoli, savoy cabbage, white cabbage, red cabbage, kohlrabi, Chinese cabbage, turnip, endive, chicory, water melon, melon, cucumber, gherkin, marrow, parsley, fennel, pea, beans, radish, black salsify, eggplant, sweet corn, pop corn, carrot, onion, tomato, pepper, lettuce, snap bean, cucurbit, shallot, broccoli, *Brassica*, and Brussels sprout. Some examples for rice include *Oryza sativa japonica, Oryza glaberrima javanica, Oryza sativa* indica, *Zizania palustris*, and hybrids thereof. The method is not restricted to these example crops.

Optionally the method comprises, subsequent to the exposure to the treatment atmosphere, one or more selected from the group consisting of: cooling, drying, and withdrawing seed from a chamber or apparatus in which the seed is located, packaging the seed, for instance in a bag or container, storing the disinfected seed, optionally at 2-10° C., coating or pelleting the seed, preferably by film coating, applying plant protection products and other additives onto the disinfected seed, planting or sowing the seed in ground or on a substrate, and growing plants from said seed.

The method for instance may comprise a further step of withdrawing the cooled and optionally dried seeds from the processing chamber or from a cooling and/or drying chamber. The method optionally further comprises packaging the seed, for instance in a bag or container. The method may further comprise storing the treated seed, optionally at 2-10° C. Possible further steps are sowing or planting the disinfected seed, germination of seed, and growing of plants from said seed, as one way of benefiting from the disinfection effect.

The method preferably comprises cooling and optionally drying the seed after the exposure to the treatment atmosphere. Drying may, for example, be performed for a time period of 2-8 hours, such as 3-6 hours, preferably 4-6 hours. This cooling and drying for example comprises exposing the seed to a cooling and a drying atmosphere. The cooling atmosphere and the drying atmosphere can be the same or different. The drying and cooling can be carried out successively or partly or completely simultaneously with each other. Preferably, the method comprises a step of combined cooling and drying and a subsequent cooling step. Combined cooling and drying for instance comprises exposure of the seed to a drying atmosphere, typically with relative humidity of 50% or less, more preferably 20% or less, and a temperature below the treatment temperature but higher than ambient, typically 30-45° C. The drying atmosphere typically is air. The final cooling step typically comprises exposure of the seed to an atmosphere with a temperature of 30° C. or less, preferably not more than 5° C. above ambient temperature, or around ambient temperature, but more preferably lower, for example 10° C. lower than ambient temperature. The cooling step preferably comprises exposure of the seed to ambient air or air cooled to typically 10-25° C. Such a final cooling step can also be applied without a combined cooling/drying step. The seed is for instance cooled to ambient temperature, or to less than 5° C. above ambient temperature, or to the storage temperature. The cooling phase is preferably carried out directly after the exposure of the seed to the treatment atmosphere. Preferably, the cooling is at least partly carried out with a cooling rate of at least 5° C./min, such as at least 10° C./min; for example in an initial cooling stage of cooling by 5-20° C. in 1 minute or less.

Preferably, the cooling phase comprises exposing the seed to an atmosphere having a temperature of 45° C. or less, in particular when the treatment atmosphere has a temperature of at least 50° C. Optionally, the end of the exposure to the treatment atmosphere is determined by the start of an exposure of the seed to a different atmosphere having a temperature up to 45° C. and/or a relative humidity of 45% or less. In case of a batch-wise treatment, cooling optionally takes place in the same chamber as where the treatment takes place, or two or more different chambers. At least the last parts of the drying and cooling phase optionally take place in a silo, bin or an external dryer or cooler.

The method optionally includes pelleting or coating disinfected seed obtained after the exposure to the treatment atmosphere and/or preferred cooling and optional drying. Such a coating may for instance protect the seeds from damage or may reduce the dust or may improve the plantability by increasing the flow characteristics. Advantageously, the coating can comprise one or more active ingredients, such as plant enhancing agents and/or plant protective products (PPPs), for example one or more selected from the group consisting of biocides, antimicrobial agent, fungicides, bactericides, insecticides, nematicides, molluscicides, acaricides, miticides, herbicides, rodenticides, pesticides, attracting agents, repellents, plant growth regulators, micronutrients, nutrients, minerals (such as potassium nitrate, magnesium sulphate, iron chelate), plant hormones, germination stimulants, pheromones, chitosan, chitine-based preparations. The coating preferably involves film coating or pelleting. A film coating typically comprises a polymeric binder. Optionally, the seed comprises a coating composition as described in WO-A-2011/028115, the complete content of which is herewith incorporated by reference.

The method may further optionally involve a priming step, for example osmotic priming, hydropriming, solid matrix priming and/or drum priming, for instance prior to the contacting with a treatment composition or subsequent to exposure to a treatment atmosphere.

The invention also relates to use of a treatment atmosphere or gaseous composition having a relative humidity of at least 50% and a temperature of at least 40° C. for enhancing the efficacy, in particular bactericidal and/or bacteriostatic efficacy, of a disinfecting agent applied to plant seed, in particular against seed-borne pathogens such as bacteria, especially against internal bacteria. Preferably, the used atmosphere or gaseous composition has a relative humidity and temperature as described hereinabove, for example 50-100° C. and at least 90%. Preferably, the use is for reactivating bacteria on said plant seed prior to the exposure of the seed to said treatment atmosphere, wherein said treatment composition preferably comprises a surfactant and/or carboxylic acid.

A further aspect of the invention relates to use of a composition comprising liquid water applied to plant seed for enhancing the disinfecting efficacy of a treatment atmosphere, as described, to which said plant seed is exposed. Yet a further aspect relates to a method for treating plant seed comprising contacting seed with a treatment composition and exposing seed to a treatment atmosphere as described, preferably providing a disinfecting effect.

The methods of the invention can be carried out in numerous types of equipment, for instance as a batch or continuous process.

An example apparatus for carrying out the method as continuous process comprises at least two chambers and transport means for transporting seed through said chambers, wherein a first chamber is suitable for contacting plant seed with a flowable treatment composition, and wherein a second chamber is suitable for maintaining a controlled atmosphere. Such flowable treatment composition includes liquid, gaseous and fluid granular compositions.

Preferably, the transport means can continuously transport seed through the chambers, such as pneumatic, gravity, fluidisation transport means and mechanic conveying means as described. The first chamber may comprise an inlet and outlet for liquid treatment composition, for instance a nozzle for spraying. The first chamber preferably comprises means for pouring/filling liquid treatment composition, and a metering unit and/or a valve for liquid treatment composition.

The apparatus can comprise a solid-liquid separator between the first and second chamber for removing excess treatment composition, for instance a centrifuge or mesh. The apparatus can comprise a heating element in the second chamber or connected for fluid to the second chamber, for providing heated vapour. The apparatus preferably comprises a third chamber for cooling and/or drying. A batch treatment can be carried out in separate chambers in which the seed is provided or in which a container containing the seed is provided, or in a single chamber capable of performing all steps.

All references cited herein are hereby completely incorporated by reference to the same extent as if each reference were individually and specifically indicated to be incorporated by reference and were set forth in its entirety herein.

The use of the terms "a" and "an" and "the" and similar referents in the context of describing the invention (especially in the context of the claims) are to be construed to cover both the singular and the plural, unless otherwise indicated herein or clearly contradicted by context. The terms "comprising", "having", "including" and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. For the purpose of the description and of the appended claims, except where otherwise indicated, all numbers expressing amounts, quantities, percentages, and so forth, are to be understood as being modified in all instances by the term "about". Also, all ranges include any combination of the maximum and minimum points disclosed and include and intermediate ranges therein, which may or may not be specifically enumerated herein.

Preferred embodiments of this invention are described herein. Variation of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject-matter recited in the claims appended hereto as permitted by applicable law. Moreover, any combination of the above-described elements in all possible variations thereof is encompassed by the invention unless otherwise indicated herein or otherwise clearly contradicted by context. The claims are to be construed to include alternative embodiments to the extent permitted by the prior art.

For the purpose of clarity and a concise description features are described herein as part of the same or separate embodiments, however, it will be appreciated that the scope of the invention may include embodiments having combinations of all or some of the features described.

The invention will now be further illustrated by the following non-limiting examples.

EXAMPLES

As treatment composition, a commercial composition TC5 for horticultural disinfection was used which comprises an aqueous solution of peracetic acid (5%) combined with hydrogen peroxide (20%). Contacting the seed with treatment composition varies from 2 to 30 min depending on solution. In some cases the solution is removed or rinsed (1 to 5 min) with water to reduce toxicity after the exposure period. Then the seed can be centrifuged or can be directly subjected to the step of exposure to the treatment atmosphere. Thereafter, seeds are dried back to original moisture content as far as necessary.

In all examples, GE is germination energy (%), Germ is final germination (%), TA is treatment atmosphere, and TC is treatment composition. The treatment compositions and surfactants used in the following examples are identified in table 13.

Example 1

General bacteria was determined by planting the seed over a semi-selective media (fungal growth suppressed) and incubated at 28° C. dark. Counts were done at day 4, 5 or 7 days and are presented as a % of bacteria infected seeds. A and B are comparative.

Table 1 shows the quality effect of the treatments on onion seed. The values are the average of two International Seed Testing Association standard tests and are given as % of germinated seed after 3 (GE) and 8 to 14 days (Final), both determined using 15° C. in dark with greenhouse test. Also shown is a value (% infected seed) for general superficial bacteria (Gen. Bact.) which was determined by planting the seed over a semi-selective media (fungal growth suppressed) and incubated at 28° C. dark. Counts were done at 5 and 7 days and presented as a % of bacteria infected seeds. Pre-treatment was with 5 wt. % TC5 (solution comprising 5 wt. % peracetic acid and 20 wt. % hydrogen peroxide, 20 times diluted). Sample C has fewer bacteria than comparative samples A and B.

TABLE 1

| | TC | TA | Avg. GE (%) | Avg. Final Germ (%) | Gen. Bact. (%) |
|---|---|---|---|---|---|
| A (comparative) | No | No | 60 | 87 | 100 |
| B (comparative) | No | Yes | 74 | 84 | 100 |
| C | TC5 | Yes | 40 | 87 | 13 |

Example 2

In example 2, *Brassica* seed was soaked for 2 min in 5% TC5, followed by 1 minute rinsing with water. The treatment atmosphere had 90% RH (relative humidity) and an exposure time of 2 minutes. Average results of 8 seed lots are shown in table 2. Herein, GE day 5 is the speed of emergence by day 5; GE final is final stand by day 7-8; Gen. Bact. general superficial bacteria, as in example 1 by day 5; CD-48 refers to the controlled deterioration or accelerated aging test for 48 hours evaluated by day 7-8; and Avg CFU: average Colony Forming Units of targeted pathogen per gram seed, evaluated after 5 days in selective media.

Sample C shows that with TC improved bacterial reduction effect was obtained compared with the TA alone. The combination results in a significant reduction of general bacteria and the specific pathogen (Xcc=*Xanthomonas campestris* pv. *campestris*) without significantly reducing the germination values or CD-values.

TABLE 2

| Sample | TC | TA | GE day 5 (%) | GE final Germ (%) | Gen. Bact. (%) | CD48 (%) | Avg Xcc (CFU/g) |
|---|---|---|---|---|---|---|---|
| A* | No | No | 93 | 95 | 92 | 72 | $3.66 \times 10^4$ |
| B* | No | Yes | 96 | 88 | 73 | 70 | $1.5 \times 10^4$ |
| C | TC5 | Yes | 86 | 86 | 33 | 60 | $2.77 \times 10^3$ |

Example 3

In example 3, the method was applied to carrot cultivars. The results as given in table 3 demonstrate the reduction of bacteria by exposure to the treatment atmosphere (RH 90%, 2 min) in combination with contacting with a treatment composition (2 min soaking in TC5 (5%), rinse with water 1 min, 30 sec centrifuge). CFU Xhc (*Xanthomonas hortorum* pv. carotae) was measured similar to example 2.

TABLE 3

| Lot | Carrot Cultivar | TC | TA | Avg. GE (%) | Avg. Final Germ (%) | General Bacteria (%) | Xhc (CFU/g) |
|---|---|---|---|---|---|---|---|
| 1 | Var #1 | TC5 | No | 21 | 89 | 100 | $6.10 \times 10^4$ |
|   |        |     | Yes | 29 | 92 | 50 | 0 |
| 2 | Var #2 |     | No | 46 | 63 | 100 | $2.10 \times 10^5$ |
|   |        |     | Yes | 20 | 78 | 63 | 0 |
| 3 | Var #3 |     | No | 56 | 66 | 100 | $2.40 \times 10^4$ |
|   |        |     | Yes | 49 | 84 | 63 | 0 |

Example 4

In example 4, the method was applied to corn salad. The results are shown in table 4. A reduction of bacteria (in particular for foci of *A. valerianellae*) was obtained by contacting with a treatment composition (2 min soaking in TC5 5%), followed by rinsing with water 1 min and 30 sec centrifuge and subsequent 2 min exposure to 90% RH treatment atmosphere. Foci=number of *Acidovorax valerianellae* infested seedlings in a group, as measured according to ISTA 7-030.

TABLE 4

| Lot | Corn salad Cultivar | TC | TA | Avg. GE | Final Germ | General Bacteria | Foci |
|---|---|---|---|---|---|---|---|
| 1 | Var #1 | TC5 | No | 92 | 92 | 100 | 11 |
|   |        |     | Yes | 84 | 97 | 60 | 2 |
| 2 | Var #1 |     | No | 72 | 75 | 100 | 12 |
|   |        |     | Yes | 61 | 76 | 100 | 0 |
| 3 | Var #1 |     | No | 80 | 81 | 100 | 29 |
|   |        |     | Yes | 41 | 80 | 85 | 0 |
| 4 | Var #2 |     | No | 95 | 94 | 100 | 7 |
|   |        |     | Yes | 96 | 97 | 100 | 0 |
| 5 | Var #3 |     | No | 95 | 93 | 100 | 31 |
|   |        |     | Yes | 93 | 91 | 78 | 0 |

Example 5

In example 5, the method was applied to water melon cultivars. The results as given in table 5 demonstrate a reduction of bacteria, obtained by 2 min soaking in TC5 5%, rinse with water 1 min, 30 sec centrifuge and subsequent 2 min exposure to a 90% RH treatment atmosphere. In particular good results are obtained for the number of plants infected with Acidovorax *citrulli*.

TABLE 5

| Lot | Watermelon Cultivar | TC | TA | Final Germ | General Bacteria | Infected plants (a) |
|---|---|---|---|---|---|---|
| 1 | A | TC5 | No | 80 | 80 | 49 |
|   |   |     | Yes | 84 | 38 | 0 |
| 2 | C |     | No | 92 | 90 | (b) |
|   |   |     | Yes | 89 | 50 |   |

(a) # Infected plants *A. citrulli*;
(b) Inconclusive

Example 6

In example 6, the method was applied to carrot seed infested with *Xanthomonas* spp. The results as given in table 6 demonstrate effective seed disinfection in combination with good germination properties. In particular, use of water (tap water) as treatment composition provides for disinfection in combination with advantageous germination properties.

In all examples, N.d. indicates that a measurement was carried out but that the number of CFU detected was below minimum value or the detection limit of 100 CFU. The skilled person understands that log CFU/10 000 seeds refers in all examples to the common logarithm (base 10), such that a decrease with 1 indicates a 10 fold reduction in CFU.

TABLE 6

|  |  | Lot 1 | | Lot 2 | | Lot 3 | |
|---|---|---|---|---|---|---|---|
| TC | TA | X spp. | Germ | X spp. | Germ | X spp. | Germ |
| None | None | 3.6 | 89.7 | 4.5 | 96.0 | 0.6 | 90.3 |
| None | Yes | n.d. | 87 | 0.1 | 91.7 | n.d. | 91.3 |
| TC6 for 2 min | Yes | n.d. | 89.3 | n.d. | 94.0 | n.d. | 90.7 |
| TC1 for 1 min | Yes | n.d. | 89.3 | — | — | n.d. | 93 |
| TC1 for 3 min | Yes | n.d. | 87.3 | n.d. | — | n.d. | 89.7 |
| TC7 for 2 min | Yes | n.d. | 78 | n.d. | — | n.d. | 87.7 |

X spp: *Xanthomonas* spp. log CFU/10 000 seeds;
Germ.: germination percentage (%) after 2 weeks.
*: comparative Example 7

In example 7, the method was applied to *Brassica* seeds infested with *Xanthomonas* spp. and *Alternaria*. The results as given in table 7 demonstrate effective disinfection in combination good germination properties. In particular good results were obtained for Xcc load in lot 2, when comparing treatment with and without treatment composition.

TABLE 7

| Lot | Tr | ET (s) | Tmp (° C.) | RH (%) | TC | GE | GC | Alt. (%) infest. | Xcc Log CFU |
|---|---|---|---|---|---|---|---|---|---|
| 1 | U* | 0 | 0 | 0 | None | 88 | 90 | 46 | 4 |
|   | A* | 120 | 65 | 90 | None | 89 | 93 | 0 | n.d. |
|   | B | 120 | 65 | 90 | TC8, 5 min | 51 | 66 | 0 | n.d. |
|   | C | 120 | 65 | 90 | TC6, 2 min | 76 | 87 | 0 | n.d. |
|   | D | 120 | 65 | 90 | TC6, 5 min | 78 | 91 | 0 | n.d. |
|   | E* | 120 | 71 | 90 | None | 86 | 90 | 0 | n.d. |
| 2 | U* | 0 |   |   | None | 83 | 85 | 40 | 4.3 |
|   | A* | 300 | 64 | 90 | None | 88 | 91 | 0.5 | 5 |
|   | B | 300 | 64 | 90 | TC8, 5 min | 20 | 24 | 0 | n.d. |
|   | C | 300 | 64 | 90 | TC6, 2 min | 85 | 89 | 0 | n.d. |

TABLE 7-continued

| Lot | Tr | ET (s) | Tmp (° C.) | RH (%) | TC | GE | GC | Alt. (%) infest. | Xcc Log CFU |
|---|---|---|---|---|---|---|---|---|---|
| | D | 300 | 64 | 90 | TC6, 5 min | 73 | 77 | 0 | n.d. |
| | E* | 300 | 70 | 90 | None | 84 | 86 | 0 | 4 |

Tr.: treatment used;
ET: exposure time (s),
Tmp: exposure temperature (° C.);
RH: relative humidity (%), all for the treatment atmosphere;
GE: germination energy;
GC: germination capacity;
Alt. inf.: seed infected with Alt.*brassicicola* (%);
Xcc: log CFU Xcc detected in 10 000 seeds.
*comparative,
n.d.: not detected Example 8

In example 8, the method was applied to *Brassica* seeds infested with *Xanthomonas* spp. Contact time with treatment composition was 20 or 30 min, as indicated in tables 8 and 9, using the formulations and process conditions as shown in table 10. The treatment atmosphere temperature was kept the same for all samples (±0.5° C.) at a temperature above 50° C.

The results as given in tables 8 and 9 demonstrate effective disinfection in combination with good germination properties.

Untreated sample 1 had severe infestation. Sample 2 shows a reduction of bacteria by soaking in water followed by 2 min exposure to the treatment atmosphere. Sample 3 with 3 min exposure time provided even better reduction of Xcc. Treatment compositions comprising a surfactant provided for lower general bacteria. The amount of general bacteria was particularly low for samples 10 and 11 with a treatment composition comprising 0.2% $H_2O_2$ and acetic acid with 0.01% Rhamnolipids. Table 9 shows that contacting the seed with treatment composition for 30 minutes provides for good reduction of Xcc CFU with a various treatment compositions.

TABLE 8

| Sample | Surfactant | TC | TC contact (min) | TA exposure time (min) | Germination (%) | General Bacteria | Xcc (CFU) |
|---|---|---|---|---|---|---|---|
| 1 | — | — | None | 0 | 91 | 100 | $1.00 \times 10^5$ |
| 2 | — | TC1 | 20 | 2 | 83 | 33 | $1.33 \times 10^4$ |
| 3 | | | 20 | 3 | 82 | 38 | $1.89 \times 10^2$ |
| 4 | S1 | | 20 | 2 | 84 | 15 | $2.77 \times 10^3$ |
| 5 | | | 20 | 3 | 84 | 23 | *N.d. |
| 6 | S2 | | 20 | 2 | 82 | 3 | $2.20 \times 10^4$ |
| 7 | | | 20 | 3 | 83 | 3 | $2.53 \times 10^3$ |
| 8 | S1 | TC2 | 20 | 2 | 83 | 5 | $5.72 \times 10^3$ |
| 9 | | | 20 | 3 | 71 | 8 | $1.82 \times 10^3$ |
| 10 | S2 | TC4 | 20 | 2 | 81 | 1 | N.d. |
| 11 | | | 20 | 3 | 83 | 1 | $7.22 \times 10^2$ |

*N.d. = not detected

TABLE 9

| Sample | Surfactant | TC | TC contact (min) | TA exposure time (min) | Germination (%) | Xcc (CFU) |
|---|---|---|---|---|---|---|
| 12 | — | — | 0 | 0 | 93 | $1.00 \times 10^5$ |
| 13 | — | TC1 | 30 | 3 | 80 | N.d. |
| 14 | S1 | TC2 | 30 | 3 | 90 | N.d. |
| 15 | | | 30 | 3 | 75 | N.d. |
| 16 | | | 30 | 3 | 71 | 96 |
| 17 | | TC3 | 30 | 3 | 81 | N.d. |
| 18 | S2 | TC2 | 30 | 3 | 75 | 100 |
| 19 | | TC3 | 30 | 3 | 77 | N.d. |

*N.d. = not detected

Example 9

In example 9, rice seed was soaked for 30 min in TC1 and TC2, followed by 30 s centrifuge. The treatment atmosphere had 90% RH (relative humidity) and an exposure time of 2.5 min. The results are shown in Table 10.

TABLE 10

| Surfactant | TC | TA | GE (%) | Final Germ (%) | Avg Aa (CFU/g) |
|---|---|---|---|---|---|
| — | No | No | 98 | 75 | $4.54 \times 10^6$ |
| No | TC1 | Yes | 93 | 88 | $9.75 \times 10^2$ |
| S2 | TC2 | Yes | 88 | 78 | $5.00 \times 10^1$ |

Example 10

In example 10, *Brassica* seed was soaked for 30 min in TC1 and TC2, followed by 30 s centrifuge. The treatment atmosphere had 90% RH (relative humidity) and an exposure time of 2.5 min. The results are shown in Table 11.

TABLE 11

| Surfactant | TC | TA | GE (%) | Final Germ (%) | Xcc (CFU/g) |
|---|---|---|---|---|---|
| — | No | No | 94 | 92 | $2.3 \times 10^6$ |
| — | TC1 | Yes | 90 | 87 | $1.5 \times 10^1$ |
| S2 | TC2 | Yes | 88 | 82 | $1.0 \times 10^0$ |

Example 11

In example 11, *Brassica* seed was soaked for 30 min in TC1, followed by 30 s centrifuge. The treatment atmosphere had 90% RH (relative humidity) and an exposure time of 2.5 min. The average results of 19 lots of *Brassica* are shown in Table 12.

TABLE 12

| TC | TA | GE (%) | Final Germ (%) | Xcc (CFU/g) |
|---|---|---|---|---|
| No | No | 88 | 87 | $1.4 \times 10^5$ |
| TC1 | Yes | 86 | 83 | 0 |

TABLE 13

| | Code | Description |
|---|---|---|
| Surfactant | S1 | DMSO 0.01% |
| | S2 | Rhamnolipids 0.01% |
| Treatment composition | TC1 | Water |
| | TC2 | ($H_2O_2$ + Peracetic acid) @ 0.2% |
| | TC3 | ($H_2O_2$ + Peracetic acid) @ 1.0% |
| | TC4 | ($H_2O_2$ + Acetic acid) @ 0.2% |
| | TC5 | ($H_2O_2$ + Peracetic acid) @ 5% |
| | TC6 | $H_2O_2$ @ 3% |
| | TC7 | $H_2O_2$ @ 10% |
| | TC8 | $H_2O_2$ @ 30% |

The invention claimed is:

1. A method for preparing disinfected seed, comprising: contacting seed having intracellular pores and/or air pockets for an exposure time of at least 10 seconds with a liquid treatment composition comprising water, and one or more disinfecting agents selected from the group consisting of acetic acid, peroxyacetic acid, and hydrogen peroxide, wherein if any peroxide is present, the total amount of peroxide is less than 20% by weight of the treatment composition;

and thereafter, while the seed intracellular pores and/or air pockets contain liquid treatment composition, exposing said seed to a treatment atmosphere for an exposure time of at least 10 seconds, wherein the treatment atmosphere has a relative humidity of at least 70% and a temperature of at least 50° C.

2. The method according to claim 1, wherein said treatment composition is supplied at a temperature of 15-40° C.

3. The method according to claim 1, wherein said treatment composition additionally comprises a surfactant.

4. The method according to claim 1, wherein said treatment atmosphere has a temperature of 50-100° C. and a relative humidity of at least 75%, and wherein said exposure time to the treatment atmosphere is up to 10 minutes.

5. The method according to claim 1, wherein said treatment composition has a pH of 6 or lower.

6. The method according to claim 1, wherein said treatment composition comprises an aqueous solution comprising a surfactant, at least 0.10 wt.% of acetic acid and at least 0.10 wt.% of hydrogen peroxide, based on total weight of the treatment composition, and wherein said treatment atmosphere has a temperature of 50-100° C. and a relative humidity of at least 80%, and wherein said exposure time to the treatment atmosphere is from 30 seconds to 10 minutes.

7. The method according to claim 1, wherein the treatment composition is supplied to the seed in an amount of at least 0.1 g seed per kg treatment composition.

8. The method according to claim 1, wherein the treatment composition is supplied to the seed in an amount providing at least 100 g water per kg seed.

9. The method according to claim 1, wherein said seed is exposed to the treatment atmosphere 24 hours or less from having contacted the seed with the treatment composition.

10. The method according to claim 1, wherein the method comprises removing at least part of the treatment composition from the seed prior to said exposing to the treatment atmosphere.

11. The method according to claim 1, wherein the seed is seed of an agricultural crop.

12. The method according to claim 1, comprising subsequent to said exposure to the treatment atmosphere, cooling and/or drying.

13. The method according to claim 1, comprising subsequent to said exposure to the treatment atmosphere, coating or pelleting the disinfected seed.

14. The method according to claim 1, wherein said treatment composition is supplied at a temperature of 20-38° C.

15. The method according to claim 1, wherein said seed is exposed to the treatment atmosphere 1 hour or less from having been contacted with the treatment composition.

16. A continuous process wherein seed having intracellular pores and/or air pockets is transported through a first chamber in which first chamber the seed is contacted for an exposure time of at least 10 seconds with a liquid treatment composition comprising water, and one or more disinfecting agents selected from the group consisting of acetic acid, peroxyacetic acid, and hydrogen peroxide, wherein if any peroxide is present, the total amount of peroxide is less than 20% by weight of the treatment composition, and said seed is thereafter, while the seed intracellular pores and/or air pockets contain liquid treatment composition, be transported through a second chamber in which second chamber the seed is exposed to a treatment atmosphere for an exposure time of at least 10 seconds, wherein the treatment atmosphere has a relative humidity of at least 70% and a temperature of at least 50° C.

* * * * *